US00PP34729P2

(12) United States Plant Patent
Williams

(10) Patent No.: US PP34,729 P2
(45) Date of Patent: Nov. 8, 2022

(54) ***COLOCASIA* PLANT NAMED 'COREDE'**

(50) Latin Name: *Colocasia esculenta*
Varietal Denomination: Redemption

(71) Applicant: Brian Paul Williams, Louisville, KY (US)

(72) Inventor: Brian Paul Williams, Louisville, KY (US)

(73) Assignee: BRIAN'S BOTANICALS, Louisville, KY (US)

( * ) Notice: Subject to any disclaimer, the term of this patent is extended or adjusted under 35 U.S.C. 154(b) by 0 days.

(21) Appl. No.: 17/541,424

(22) Filed: Dec. 3, 2021

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP23,896 P2 * 9/2013 Cho ..... A01H 6/10
Plt./373

* cited by examiner

*Primary Examiner* — Karen M Redden
(74) *Attorney, Agent, or Firm* — Penny J. Aguirre

(57) ABSTRACT

A new cultivar of *Colocasia* plant named 'Corede' that is characterized by its corrugated foliage with a reflective sheen, its black foliage with bright pink mid-veins, its petioles that are dark maroon-black in color, its plant height of 1.2 to 1.5 m, and its clumping plant habit.

2 Drawing Sheets

Botanical classification: *Colocasia esculenta.*
Cultivar designation: 'Corede'.

BACKGROUND OF THE INVENTION

The present invention relates to a new and distinct cultivar of *Colocasia esculenta* and will be referred to hereafter by its cultivar name, 'Corede'. 'Corede' represents a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Colocasia* plants with unique foliage coloration and distinctive leaf veins.

'Corede' arose from a cross made in June of 2017 between unnamed and unpatented *Colocasia esculenta* plants from the Inventor's breeding program as both the female and male parents. 'Corede' was selected as a single unique plant in August of 2018 from amongst the seedlings derived from the above cross.

Asexual propagation of the new cultivar was first accomplished by root cuttings by the Inventor in Louisville, Ky. in August of 2018. Asexual propagation by root cuttings and tissue culture using meristematic tissue has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Corede' as a new and unique cultivar of *Colocasia.*

1. 'Corede' exhibits corrugated foliage with a reflective sheen.
2. 'Corede' exhibits a black foliage with bright pink mid-veins.
3. 'Corede' exhibits petioles that are dark maroon-black in color.
4. 'Corede' exhibits a plant height of 1.2 to 1.5 m.
5. 'Corede' exhibits a clumping plant habit.

The female parent of 'Corede', differs from 'Corede' in having a shorter plant height and foliage that lacks pink veins. The male parent of 'Corede', differs from 'Corede' in having green foliage with white veins and maroon-red petioles, and in producing runners (not clump-forming). 'Corede' can be most closely compared to the *Colocasia* cultivars 'Black Sapphire Gecko' (U.S. Plant Pat. No. 27,966) and 'Nancy's Revenge' (not patented). 'Black Sapphire Gecko' is similar to 'Corede' in having heart shaped foliage and dark black-maroon petioles. 'Black Sapphire Gecko' differs from 'Corede' in having foliage that is all black in color and lacks pink veins and foliage that is less corrugated and ruffled. 'Nancy's Revenge' is similar to 'Corede' in having heart shaped foliage and a clumping habit. 'Nancy's Revenge' differs from 'Corede' in having green foliage with white mid-veins.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Brian's Botanicals, Plants Nouveau; the breeder's representative for licensing UTube, and Facebook.

BRIEF DESCRIPTION OF THE DRAWINGS

The accompanying color photographs illustrate the overall appearance and distinct characteristics of the new *Colocasia*, 'Corede'. The photographs were taken of 2 year-old plants as grown outdoors in a trial garden, in full sun, under 2 mm poly in Louisville, Ky.

The photograph in FIG. 1 provides an overall view of the mature foliage and plant habit of 'Corede'.

Figure 1:
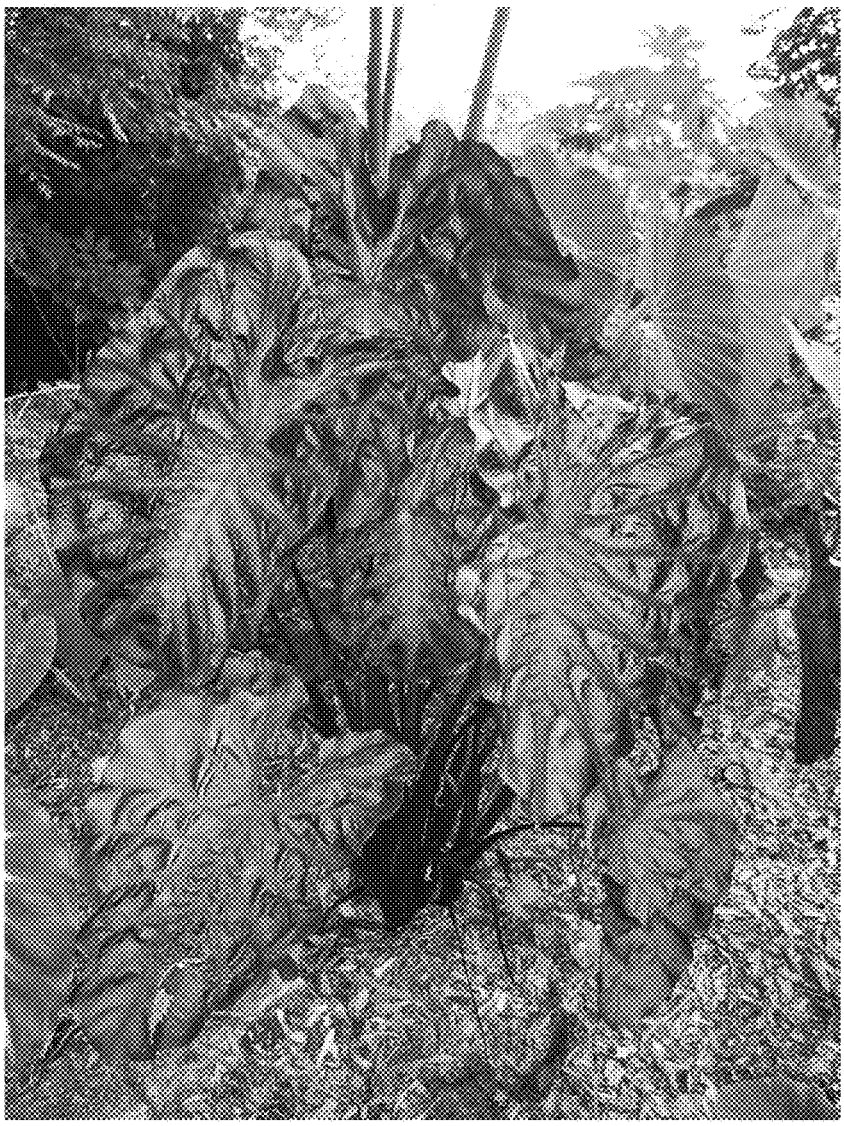
Figure 2:
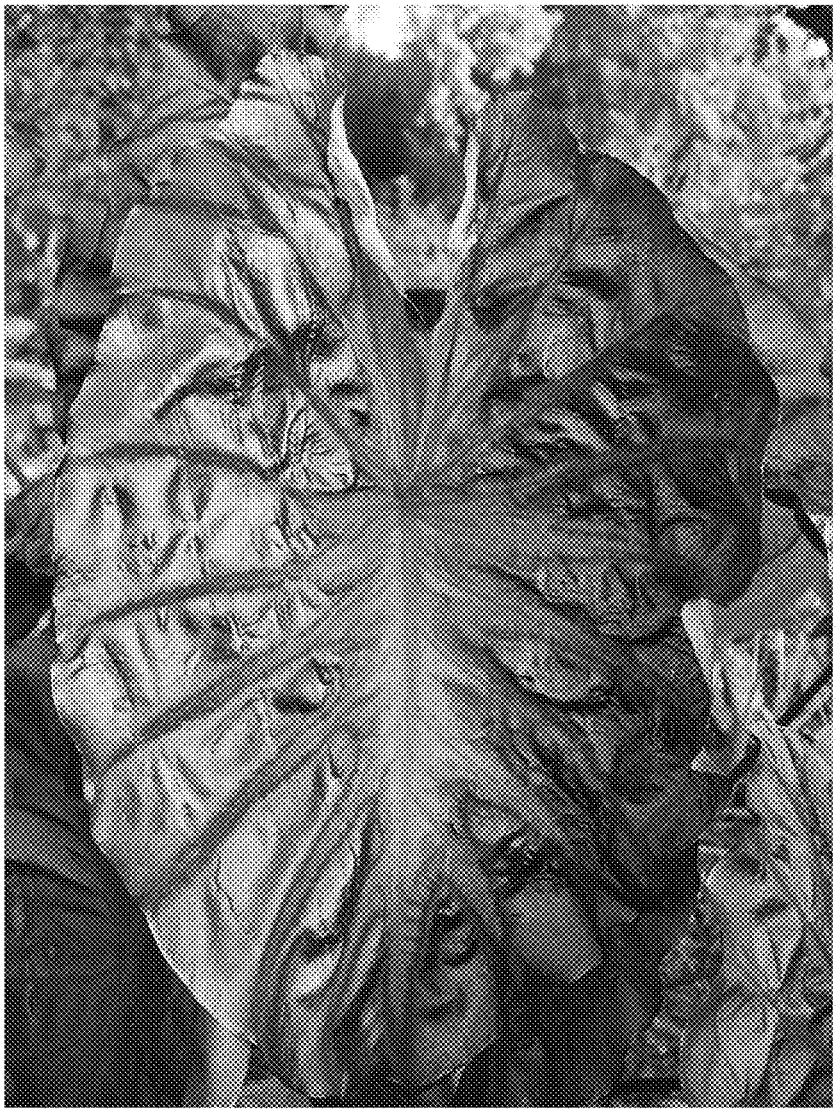

The photograph in FIG. 2 provides a close-up view of the upper leaf surface of 'Corede'.

The colors in the photographs are as close as possible with the digital photography techniques available, the color values cited in the detailed botanical description accurately describe the colors of the new *Colocasia*.

DETAILED BOTANICAL DESCRIPTION OF THE PLANT

The following is a detailed description of a division from a 2-year-old plant of the new cultivar plants as grown outdoors, in full sun, under 2 mm poly in Louisville, Ky. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Periodically throughout the year depending on temperatures in Kentucky.

*Plant type.*—Tropical perennial herb.

*Plant habit.*—Upright, stemless, clump forming.

*Height and spread.*—Average of 77 cm in height and 48 cm in width, mature plant in the landscape reaches 1.2 m to 1.5 m in height and 1.2 m in width.

*Hardiness.*—U.S.D.A. Zones 7 to 10.

*Diseases and pests.*—No resistance and susceptibility to diseases or pests has been observed.

*Roots.*—Fleshy, no runners, color; NN155D, flushed with N78A.

*Propagation type.*—Root cuttings and tissue culture.

*Root development.*—3 to 5 weeks for root initiation and 3 to 6 weeks to produce a young plant from a rooted cutting.

*Growth rate.*—Vigorous.

*Stem description.*—Stemless, can produce large corms with age.

*Corm description.*—Fleshy, matte, overall globose oval in shape, an average of 3 cm in length, 5 cm in diameter, color; 174A.

Foliage description:

*Leaf shape.*—Oval.

*Leaf division.*—Single.

*Leaf base.*—Cordate.

*Leaf apex.*—Broadly acute.

*Leaf venation.*—Pinnate, young leaves; upper surface 145D, outside edges of veins flushed with 187A, lower surface 145D, flushed with 183A, mature leaves; upper surface matches surface color, lower surface N77A.

*Leaf margins.*—Smooth and very undulate, a blend of 202A and N187A in color.

*Leaf attachment.*—Petiolate.

*Leaf arrangement.*—Emerges from tuber.

*Leaf surface.*—Upper surface and lower surface; coriaceous, glabrous, corrugated, develops a reflective sheen.

*Leaf orientation.*—Held horizontal to downward and cupped.

*Leaf color.*—Young foliage upper surface; 149A and 145A, center 145C, lightly flushed around outside edges with 202A, young surface lower surface; 144A, flushed around the outer edges with a blend of N187A and 187A, mature foliage upper surface; N186A, center and spreading over the veins 71A, mature foliage lower surface: N92A, center N77B.

*Leaf size.*—An average of 31 cm in length and 21 cm in width.

*Petioles.*—Held erect to semi-erect, an average of 52 cm in length and 1 cm in distal diameter and 3 cm in proximal diameter, glabrous and matte surface, young color; mottled, NN155A and 185A, mature color; 187A.

Inflorescence description:

*Inflorescence type.*—Spadix surrounded by a spathe, male portion held above female portion, only female flowers are developed.

*Inflorescence size.*—An average of 21 cm in length and 2 cm in width.

*Inflorescence bud.*—Linear in shape, an average of 13 cm in length and 1 cm in width.

*Flower fragrance.*—None.

*Lastingness of inflorescence.*—Inflorescence blooms intermittently during the bloom period, individual flowers last about 2 to 3 weeks.

*Inflorescence/flower quantity.*—An average of 40 female flowers sessile to spadix, sessile male flowers are undeveloped.

*Spathe.*—Hooded, bract, subtending spadix, an average of 18.5 cm in length and 3.5 cm in width, entire and slightly undulate margin, bottom portion; flattened rotund shape, an average of 2.8 cm in length and 3.1 cm in width, apex fused to upper portion, upper portion (hood); elongated oval in shape, an average of 12 cm in length and 3 cm in width, acute apex, upper and lower portion inner and outer surface; coriaceous, smooth, and glabrous, color; outer surface a blend of 182A and 182B, inner surface 160A.

*Spadix.*—Male portion above female zone, upright linear to slightly narrow oblanceolate in shape (phallus like), apex bluntly pointed, an average of 5 cm in length, male portion; an average of 4.5 cm in length and 5 mm in width, female portion; an average of 5 mm in length and 2 mm in width, color; male portion, 187A female 161A.

*Peduncle.*—Grows from base of plant, flattened in shape, an average of 17.5 cm in length and 1.3 cm in diameter, durable and strong, 187A in color, matte, glabrous and smooth surface.

Reproductive organs:

*Gynoecium.*—1 pistil with sessile, discoid stigmas; 159C in color, single ovary with many minute ovules; oval in shape and translucent in color.

*Androcoecium.*—Undeveloped.

*Fruit and seed.*—Sterile.

It is claimed:

1. A new and distinct cultivar of *Colocasia* plant named 'Corede' as herein illustrated and described.

* * * * *